(12) United States Patent
Ricotti et al.

(10) Patent No.: US 9,243,967 B2
(45) Date of Patent: Jan. 26, 2016

(54) SENSOR FOR PRESSURE MEASUREMENTS

(71) Applicant: STMICROELECTRONICS S.R.L., Agrate Brianza (MB) (IT)

(72) Inventors: Giulio Ricotti, Broni (IT); Juri Giovannone, Cernobbio (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 310 days.

(21) Appl. No.: 13/941,893

(22) Filed: Jul. 15, 2013

(65) Prior Publication Data
US 2014/0020473 A1    Jan. 23, 2014

(30) Foreign Application Priority Data

Jul. 18, 2012 (IT) .............. TO2012A0633

(51) Int. Cl.
| | | |
|---|---|---|
| G01L 7/00 | (2006.01) | |
| G01L 9/02 | (2006.01) | |
| G01L 9/00 | (2006.01) | |
| G01L 1/20 | (2006.01) | |
| G01L 1/22 | (2006.01) | |
| D03D 1/00 | (2006.01) | |
| H01C 17/02 | (2006.01) | |
| A43B 3/00 | (2006.01) | |
| A43D 1/02 | (2006.01) | |
| D03D 9/00 | (2006.01) | |
| D03D 13/00 | (2006.01) | |
| D03D 15/00 | (2006.01) | |
| A61B 5/103 | (2006.01) | |
| A61B 5/00 | (2006.01) | |

(52) U.S. Cl.
CPC .............. *G01L 9/02* (2013.01); *A43B 3/0005* (2013.01); *A43D 1/025* (2013.01); *D03D 1/0088* (2013.01); *D03D 9/00* (2013.01); *D03D 13/008* (2013.01); *D03D 15/0094* (2013.01); *G01L 1/205* (2013.01); *G01L 1/22* (2013.01); *G01L 9/0002* (2013.01); *H01C 17/02* (2013.01); *A61B 5/1038* (2013.01); *A61B 5/6807* (2013.01); *A61B 2562/0247* (2013.01); *D10B 2401/18* (2013.01); *Y10T 29/49087* (2015.01)

(58) Field of Classification Search
None
See application file for complete search history.

(56) References Cited

U.S. PATENT DOCUMENTS

| | | | | |
|---|---|---|---|---|
| 3,686,926 A | * | 8/1972 | Miller et al. ................. | 73/61.72 |
| 3,953,640 A | * | 4/1976 | Takada .......................... | 428/188 |
| 4,196,245 A | * | 4/1980 | Kitson et al. ................. | 428/198 |
| 7,122,152 B2 | * | 10/2006 | Lewis et al. .................... | 422/50 |
| 7,544,627 B2 | * | 6/2009 | Tao et al. ....................... | 442/189 |
| 7,770,473 B2 | * | 8/2010 | Von Lilienfeld-Toal et al. .......................... | 73/862.68 |

(Continued)

FOREIGN PATENT DOCUMENTS

| | | |
|---|---|---|
| DE | 102010023892 A1 | 8/2011 |
| EP | 2040053 A1 | 3/2009 |
| EP | 2362421 A1 | 8/2011 |

*Primary Examiner* — Peter Macchiarolo
*Assistant Examiner* — Jermaine Jenkins
(74) *Attorney, Agent, or Firm* — Allen, Dyer, Doppelt, Milbrath & Gilchrist, P.A.

(57) ABSTRACT

A sensor for pressure measurement may include a fabric support, an electrically conductive structure including tracks on the fabric support having resistance variations in response to deformations thereof, and a processor coupled to the electrically conductive structure and configured to sense resistance values of respective tracks of the electrically conductive structure and to provide a signal representative of a pressure difference across opposite faces of the fabric support.

29 Claims, 6 Drawing Sheets

(56) References Cited

U.S. PATENT DOCUMENTS

| | | |
|---|---|---|
| 8,283,657 B2 | 10/2012 | La Rosa et al. |
| 8,981,792 B2 | 3/2015 | Girlando |
| 2007/0171024 A1 | 7/2007 | Yang et al. |
| 2009/0033467 A1 | 2/2009 | Finocchiaro et al. |
| 2011/0048123 A1* | 3/2011 | Chocron ............... G01L 5/0052 73/159 |
| 2011/0211316 A1 | 9/2011 | La Rosa |
| 2012/0132711 A1 | 5/2012 | La Rosa et al. |

* cited by examiner

SENSOR FOR PRESSURE MEASUREMENTS

TECHNICAL FIELD

The present disclosure relates to a sensor for pressure measurements.

BACKGROUND

In some applications, there may be a need to determine, in an accurate way, pressure values over rather extensive regions, the surface of which may be of the order of square centimeters or square meters. For example, in some fluidic filters, it is useful to have a measurement of the pressure exerted by the fluid that is treated in order to monitor the operating conditions of the fluid itself. In a different field, the use of pressure sensors incorporated in the innersole of footwear enables data to be obtained regarding the distribution of the weight of the user on the sole of his foot, both for clinical assessments (evaluation and correction of posture and gait) and for other purposes that may be of interest for the user (for example, for providing a pedometer function).

When there are requirements of this sort, usually an array of independent point sensors is employed, which provides information on the pressure exerted in a given and limited area. However, such approaches of this type may not always satisfactory. In many cases, in fact, positioning of discrete sensors is problematical, if not impossible, and in any case more often than not there is the problem of the wired connection with the detection circuitry. In some cases, as in the case of fluidic filters, the very presence of the sensors may cause unacceptable disturbance.

SUMMARY

An object is to provide a sensor for pressure measurements that provides an approach to the limitations described.

An aspect is directed to a sensor for pressure measurement. The sensor may comprise a fabric support, at least one electrically conductive structure comprising a plurality of tracks on the fabric support having resistance variations in response to deformations thereof, and a processor coupled to the at least one electrically conductive structure and configured to sense resistance values of respective tracks of the at least one electrically conductive structure and to provide a signal representative of a pressure difference across opposite faces of the fabric support.

BRIEF DESCRIPTION OF THE DRAWINGS

For a better understanding of the invention, some embodiments thereof will now be described, purely by way of non-limiting example and with reference to the attached drawings, wherein.

DETAILED DESCRIPTION OF THE PREFERRED EMBODIMENTS

Figure 1:
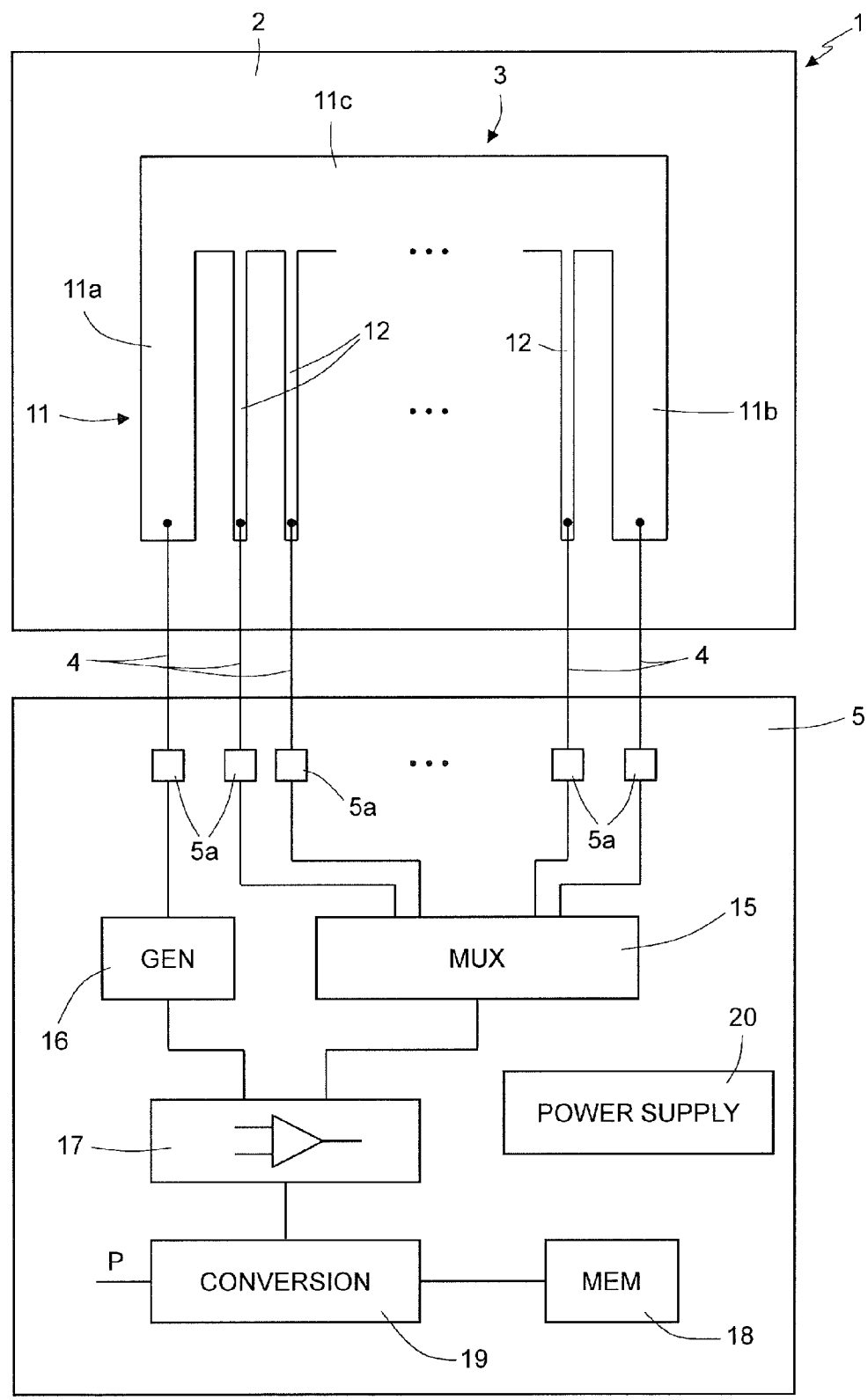
FIG. 1 is a schematic block diagram of a sensor for pressure measurements, according to an embodiment of the present disclosure.

With reference to FIG. 1, a sensor 1 for pressure measurements according to one embodiment is now described. The sensor 1 comprises a support 2, a conductive structure 3 on the support 2, wired-connection lines 4, and a processing unit 5. The support 2, a portion of which is illustrated in greater detail in FIG. 2, comprises a fabric having warp yarns 7 and weave yarns 8, woven so as to define a plurality of meshes 10. The warp yarns 7 and the weave yarns 8 comprise a dielectric material, for example, a non-conductive polymer, such as polyimide or nylon.

The materials and diameter and density of the warp yarns 7 and of the weave yarns 8 are selected according to the application of the sensor 1 so as to bestow on the support 2 a controlled longitudinal elastic modulus in the warp direction DWRP and in the weave direction DWV, and moreover, obtain meshes 10 of the desired dimensions. In one embodiment, the warp yarns 7 and the weave yarns 8 are of one and the same material, have the same diameter, and have a uniform density. Consequently, the meshes 10 have the same dimensions, and the support 2 presents isotropic behavior because the longitudinal elastic modulus is substantially the same in the warp direction DWRP and in the weave direction DWV.

Figure 4:
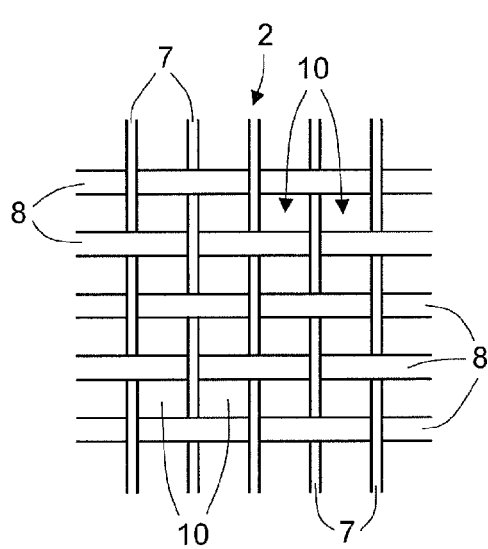

The densities of the warp yarns 7 and of the weave yarns 8 may, however, not be the same as one another (as shown in FIG. 4) and, moreover, not be uniform. Since the longitudinal elastic modulus, given the same diameter and material of the yarns, is basically determined by the density of the yarns themselves, the response to tensile stress (due, in particular, to a difference in pressure across opposite faces of the support 2) is different in the warp direction DWRP and in the weave direction DWV.

In the case of non-uniform density of the yarns, the support 2 has regions with thicker warp yarns 7 and/or weave yarns 8, and meshes 10 of smaller dimensions and regions with sparser warp yarns 7 and/or weave yarns 8 and meshes 10 of larger dimensions. Moreover, the longitudinal elastic modulus and the response to tensile stress are variable according to the density of the yarns.

Figure 5:
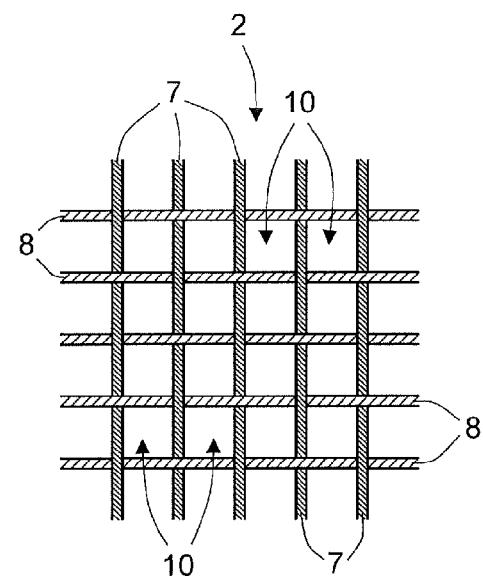

An anisotropic behavior of the support 2 as regards the longitudinal elastic modulus may be obtained also using warp yarns 7 of a different diameter from the weave yarns 8 (FIG. 4), or else different materials for the warp yarns 7 and for the weave yarns 8 (FIG. 5). The conductive structure 3 is formed on a face of the support 2 and comprises a plurality of metal tracks configured so as to provide resistance variations in response to variations of length. For example, the conductive structure 3 may comprise nickel, copper, or aluminum. In one embodiment, in particular, the conductive structure 3 comprises a reference track 11 and a plurality of sense tracks 12. The reference track 11 has two parallel sections 11a, 11b arranged in the warp direction DWRP, joined at respective first ends by a transverse section 11c, oriented in the weave direction DWV. Second ends of the sections 11a, 11b are connected to respective terminals 5a of the processing unit 5 through connection lines 4. The reference tracks 12 are arranged parallel to one another and extend in comb like fashion from the section 11c of the reference track 11 in the warp direction DWRP. In one embodiment, the sense tracks 12 are all the same as one another. Free ends of the sense tracks 12 are connected to respective terminals 5a of the processing unit 5 through connection lines 4.

The reference track 11 and the sense tracks 12 have respective lengths and widths, such as to cause resistance variations in response to deformations due to pressure differences across the faces of the support 2. In one embodiment, in particular, the sense tracks 12 have all the same dimensions and the same response in terms of resistance variations.

In one embodiment, the processing unit 5 is provided in a semiconductor chip set outside the support 2. Moreover, the processing unit 5 is configured to detect resistance values associated with the sense tracks 12 and, possibly, with the reference track 11 and to provide pressure measurements starting from the resistance values detected. In one embodiment, the resistance values of the sense tracks 12 and of the reference track 11 are sequentially detected, in rotation.

In greater detail, the processing unit 5 comprises a multiplexer 15, a generator 16, a detector module 17, a memory module 18, a conversion module 19, and a power-supply source 20. The multiplexer 15 connects the detection module 17 in rotation selectively to one of the terminals 5a coupled to the sense tracks 12, using for this purpose a clock signal not shown in FIG. 1. In one embodiment, the detection module 17 is connected by the multiplexer 15 also to the terminal 5a coupled to the section 11c of the reference track 11.

The generator 16 provides an electrical supply, for example, a current IT, to the reference track 11, which functions as common terminal for the conductive structure 3. The detection module 17 detects a voltage produced in response to the current IT and uses it for detecting a resistance value associated to the sense track 12 selected by the multiplexer 15 (or, possibly, to the reference track 11), according to the configuration of the multiplexer 15.

The conversion module 19 determines a pressure measurement for the reference track 11 or the sense track 12 selected, using the resistance value detected and a calibration table C stored in the memory module 18. The power-supply source 20 collects energy from the surrounding environment and converts it into electrical energy for supplying the processing unit 5. According to the type of application for which the sensor 1 is used, the power-supply source may be based, for example, on piezoelectric, thermoelectric, or photovoltaic elements. Alternatively, the power-supply source 20 may be a battery.

The sensor 1 described may present numerous advantages. In the first place, it is possible to obtain in a simple and low-cost way sensors with a rather extensive surface. The support 2 of dielectric fabric, in particular, polymeric fabric, may be produced without difficulty in pieces of various size, even of several square meters. The conductive structure 3 may be obtained by dipping the support in a galvanic bath and then carrying out a laser ablation, for removing the unnecessary metal. Alternatively, techniques of direct deposition along a track may be used.

The conductive structure 3 described moreover may enable association of information of position to the measurements made by simply keeping track of which reference tracks 11 or sense tracks 12 are each time connected to the detection module 17 through the multiplexer 15. Consequently, in addition to average detections, the sensor 1 may provide also local pressure measurements.

Reading in rotation the reference tracks 11 and the sense tracks 12 with the multiplexer 15 enables optimization of the use of electronic components in the processing unit 5 according to the requirements of the individual application. The processing unit 5 may in fact be shared by a relatively high number of reference tracks 11 or sense tracks 12 (for example, 128 or 256).

In addition to the evident advantages in terms of dimensions and consumptions of the sensor, it is possible to use processing units with high performance, without affecting the cost significantly. A further advantage resides in that the fabric forming the support 2 is permeable to fluids to an extent depending upon the density of the warp and weave yarns. This enables broadening of the range of possible uses of the sensor 1 and inclusion of applications, for example, in the fluidic field.

Figure 6:
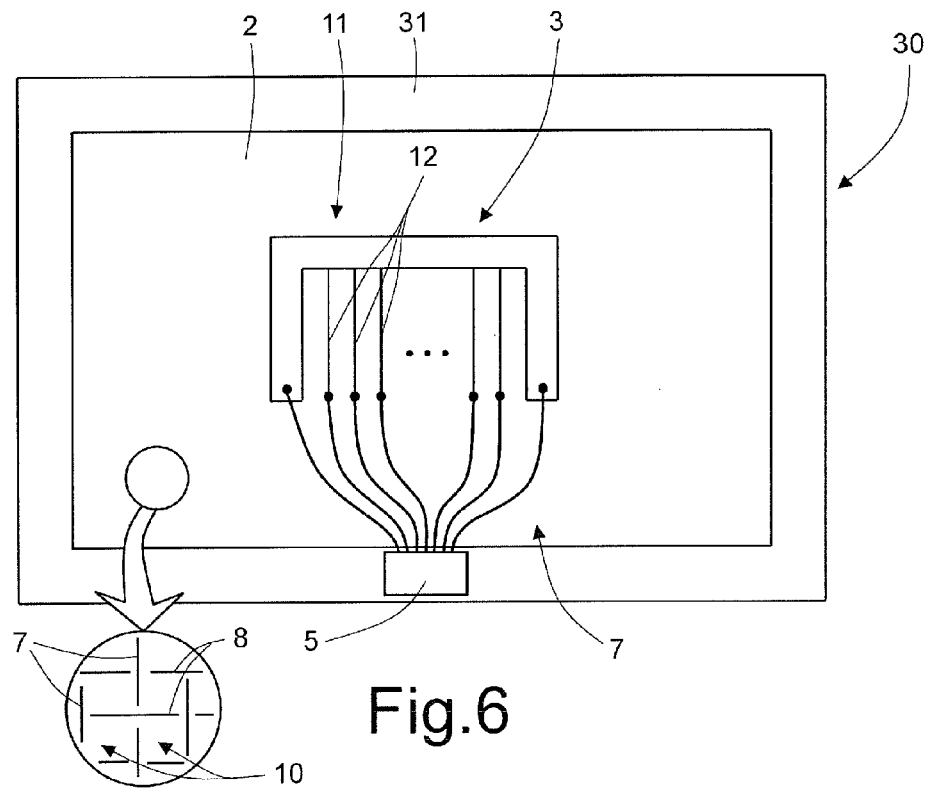
FIG. 6 is a schematic block diagram of a fluidic device incorporating the sensor of FIG. 1.

In the embodiment illustrated in FIG. 6, the sensor for pressure measurements 1 is used in a fluidic filter 30. In this case, the margins of the support 2 are fixed to a frame 31, to which also the processing unit 5 is fitted. The conductive structure 3 is located at the center with respect to the frame 31. The density of the warp yarns 7 and of the weave yarns 8 and the dimensions of the meshes 10 are determined according to the characteristics that the filter 30 must present, i.e., according to the minimum dimensions of the particles that must be removed from the flow traversing the filter 30 itself.

Figure 7:
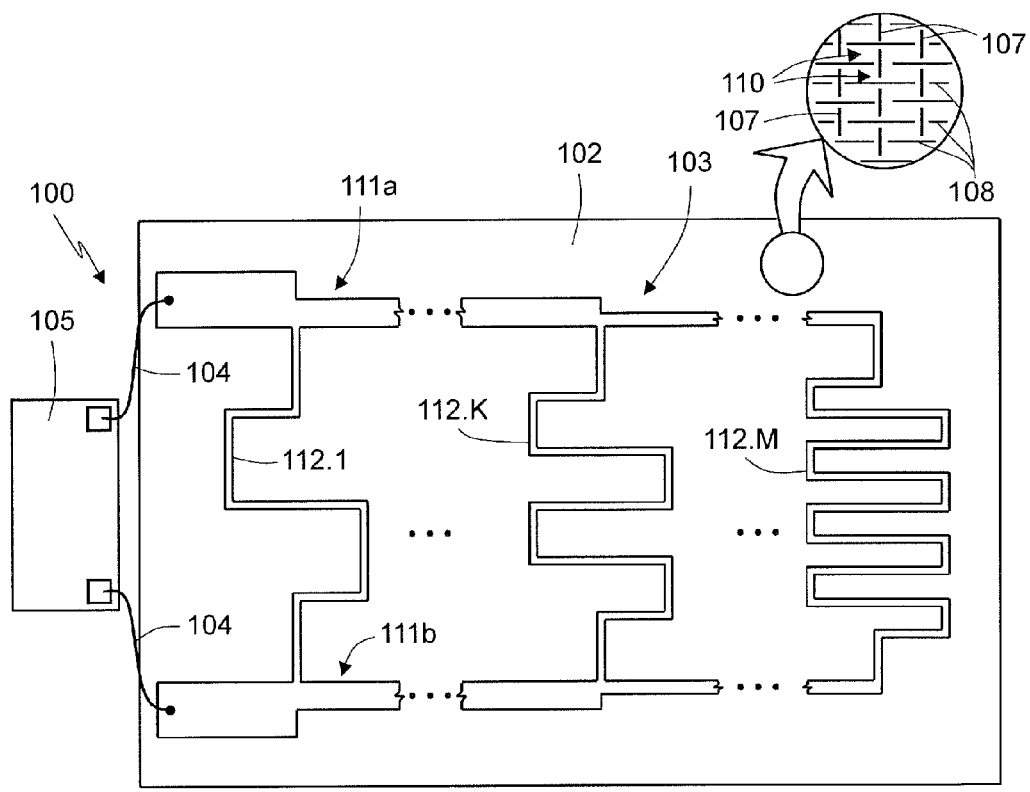
FIG. 7 is a schematic block diagram of a sensor for pressure measurements, according to another embodiment of the present disclosure.

In the embodiment shown in FIG. 7, a sensor for pressure measurements 100 comprises a support 102 of insulating polymeric fabric, a conductive structure 103, arranged on the support 102, and a processing unit 105, connected to the conductive structure 103 through wired-connection lines 104. The support 102 comprises warp yarns 107 and weave yarns 108 having the same diameter, woven so as to form meshes 110. In one embodiment, the density of the weave yarns 108 is higher than the density of the warp yarns 107 so that the longitudinal elastic modulus of the support 102 is greater in the weave direction DWV than in the warp direction DWRP.

The conductive structure 103 is made in the form of a resistive ladder network, with two connection tracks 111a, 111b parallel to one another (for example, oriented in the weave direction DWV) and sense tracks 112.1, ..., 112.M. Ends of the connection tracks 111a, 111b define terminals of the conductive structure 103 and are connected to respective terminals of the processing unit 105.

The sense tracks 112.1, ..., 112.M each has opposite ends respectively connected to the connection tracks 111a, 111b and are arranged at respective locations in the weave direction DWV. The sense tracks 112.1, ..., 112.M extend along respective polygonal serpentine tracks with numbers of bends N1, ..., NM and have respective distinct rest resistance values R1, ..., RM. For the generic sense track 112.K, the rest resistance value RK is determined by the overall width WK and length (which in turn depends upon the length LK of the individual serpentine sections and upon the number of bends NK). In one embodiment, the connection tracks 111a, 111b have sections with respective different resistance values, for example, increasing from the sense track 112.1 to the sense track 112.M.

Figure 8:
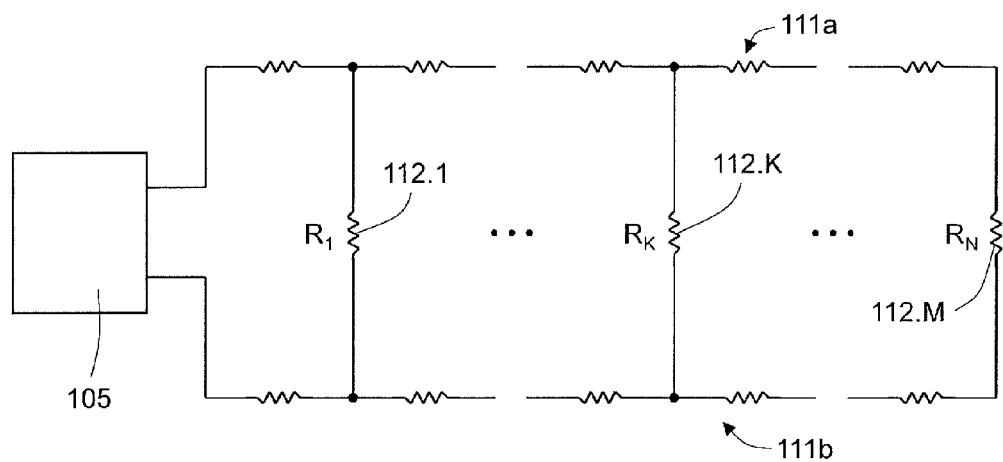
FIG. 8 is an electrical diagram of the sensor of FIG. 7.

FIG. 8 shows an electrical equivalent of the conductive structure 103. The conductive structure 103 is configured in such a way that, as the difference in pressure across the faces of the support 102 varies in an operating range, the sense tracks 112.1, ..., 112.N cause, across the terminals of the conductive structure 103, respective resistance variations DR1, ..., DRM falling in respective distinct and non-overlapping intervals I1, ..., IM (for example, spaced apart in geometrical progression).

Figure 9:
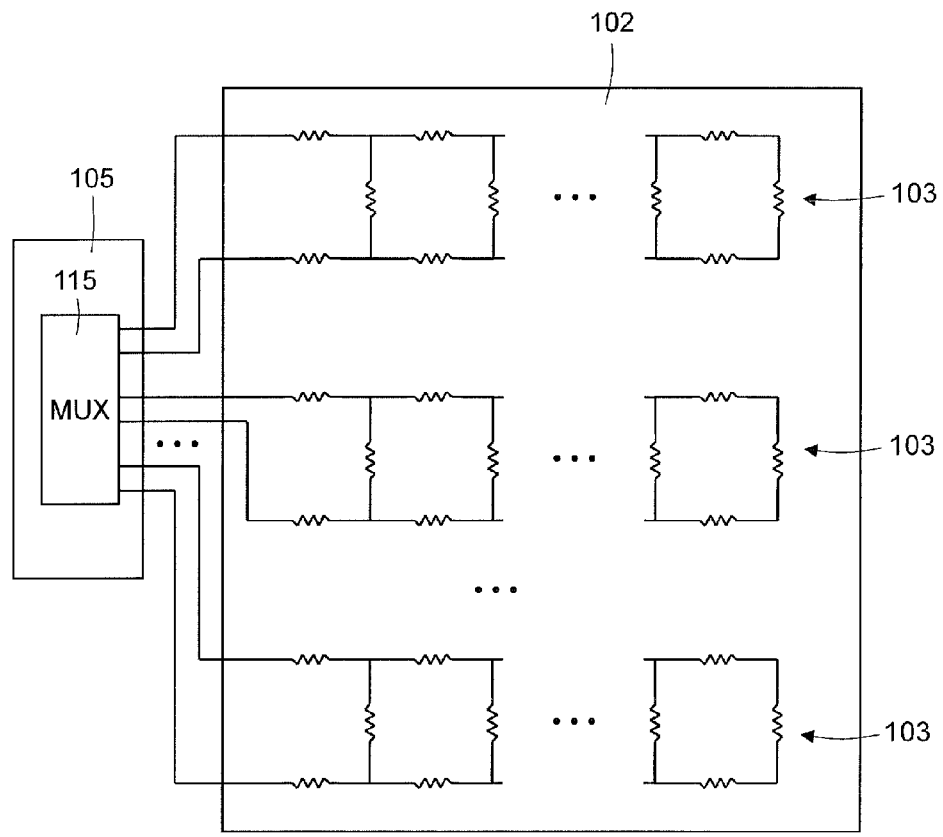
FIG. 9 is a schematic circuit diagram of a sensor for pressure measurements, according to another embodiment of the present disclosure.

In this way, using a plurality of conductive structures 103 that extend on one and the same support 102 in the weave direction DWV and aligned in the warp direction DWRP, as shown in FIG. 9, it is possible to obtain two-dimensional information on the distribution of pressure on the sensor. In particular, it is possible to determine the position of pressure anomalies confined in a restricted region. The resistance values of the conductive structures 103 may be in fact determined in rotation, using a multiplexer 115 in the processing unit 105. First information of position (in the warp direction DWRP) may be derived from the order of reading of the conductive structures 103, identifying the specific conductive structure 103 selected by the multiplexer 115. Second information of position, regarding the weave direction DWV, may be obtained by determining in which of the intervals I1, ..., IM the resistance variation (with respect to the value at rest) detected for the conductive structure 103 selected for reading is comprised. As explained above, the intervals I1, ..., IM are associated in a unique way to respective sense tracks 112.1, ..., 112.M of the conductive structure 103 selected for reading. Since the sense tracks 112.1, ..., 112.M correspond to respective locations in the weave direction DWV, the pressure variations may be located.

The two-dimensional information of position may be exploited, for example, in a fluidic filter for evaluating onset of anomalous conditions or any malfunctioning, which could be due to turbulence in the flow or to soiling of the filter itself. Both the turbulence and occlusion of an area of the filter, in fact, determine local pressure variations and hence a different response of the sense tracks 112.1, ..., 112.N of one and the same conductive structure 103, according to their position.

Figure 10:
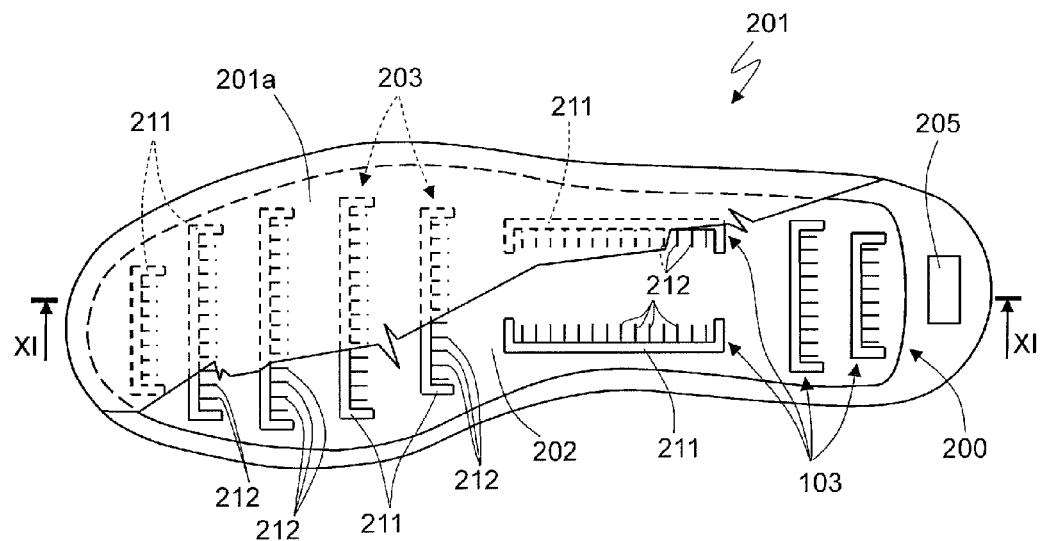
FIG. 10 shows a top plan view of a portion of an item of footwear incorporating a sensor for pressure measurements, according to another embodiment of the present disclosure.
Figure 11:
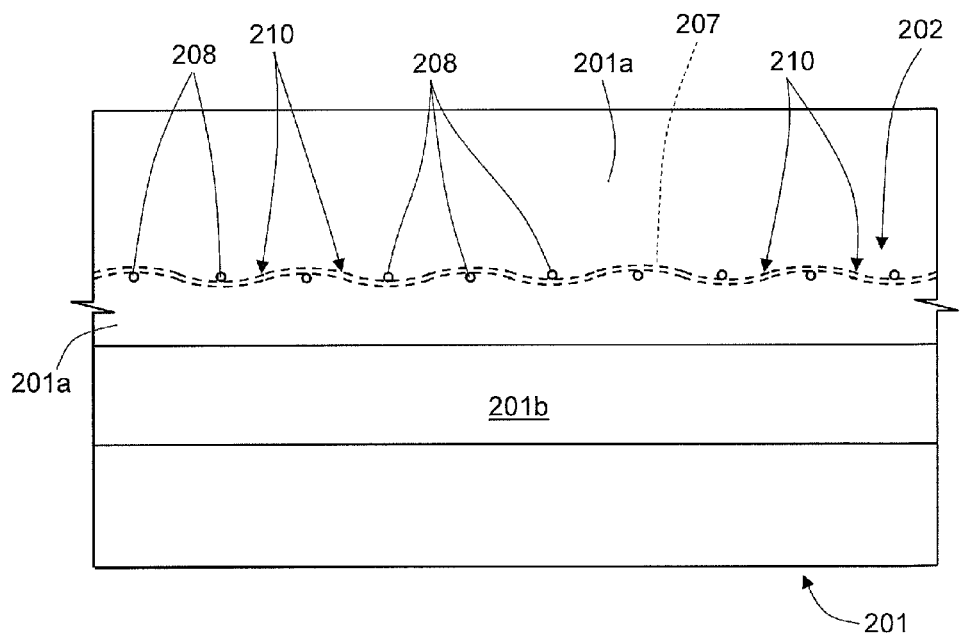
FIG. 11 is an enlarged cross-sectional view through a portion of the item of footwear of FIG. 10, taken along the line XI-XI of FIG. 10.

FIGS. 10 and 11 illustrate another embodiment. In this embodiment, a sensor for pressure detection 200 is embedded in the innersole 201 of an item of footwear (not shown entirely). At least one layer 201a of the innersole 201 is of elastomeric material and, in the example described, has a chamber 201b for absorption of vibrations and impact.

The sensor 200 comprises a support 202 of insulating polymeric fabric, arranged on which are conductive structures 203, and a processing unit 205. The support 202 is embedded in the layer 201a of elastomeric material and comprises warp yarns 207 and weave yarns 208 forming meshes 210. The density of the warp yarns 207 and of the weave yarns 208 is selected so as to enable the material of which the layer 201a is made to penetrate across the meshes 210 during molding.

Figure 2:
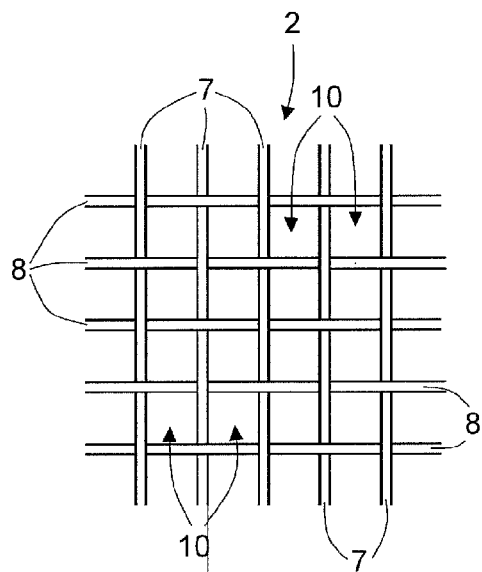
FIG. 2 shows an enlarged view of the sensor of FIG. 1.
Figure 3:
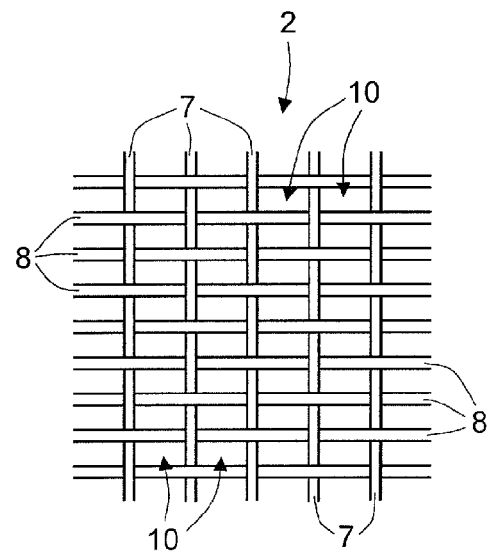
FIGS. 3-5 are enlarged views of other embodiments of the sensor of FIG. 2.

The conductive regions 203 each comprises a reference track 211 and sense tracks 212, substantially as already described in relation to FIGS. 1 and 2, and are connected to the processing unit 205, which is also embedded in the layer 201a of elastomeric material and is provided with a multiplexer (not shown). The conductive regions 203 are arranged so that the sense tracks are thicker in the portions of innersole where the higher and more significant loads are expected (for example, the heel and the forefoot).

The support 202 of fabric with meshes 210 of appropriate size is advantageously covered by the material forming the layer 201a. The sensor 200 is hence withheld precisely in place, and any sliding due to use, which would be instead more likely with the support of a sheet material, is prevented. Any detection regarding posture and gait of the user is thus always accurate. The chamber 201b may favor stretching out of the warp and weave yarns when the innersole 201 is under load.

Figure 12:
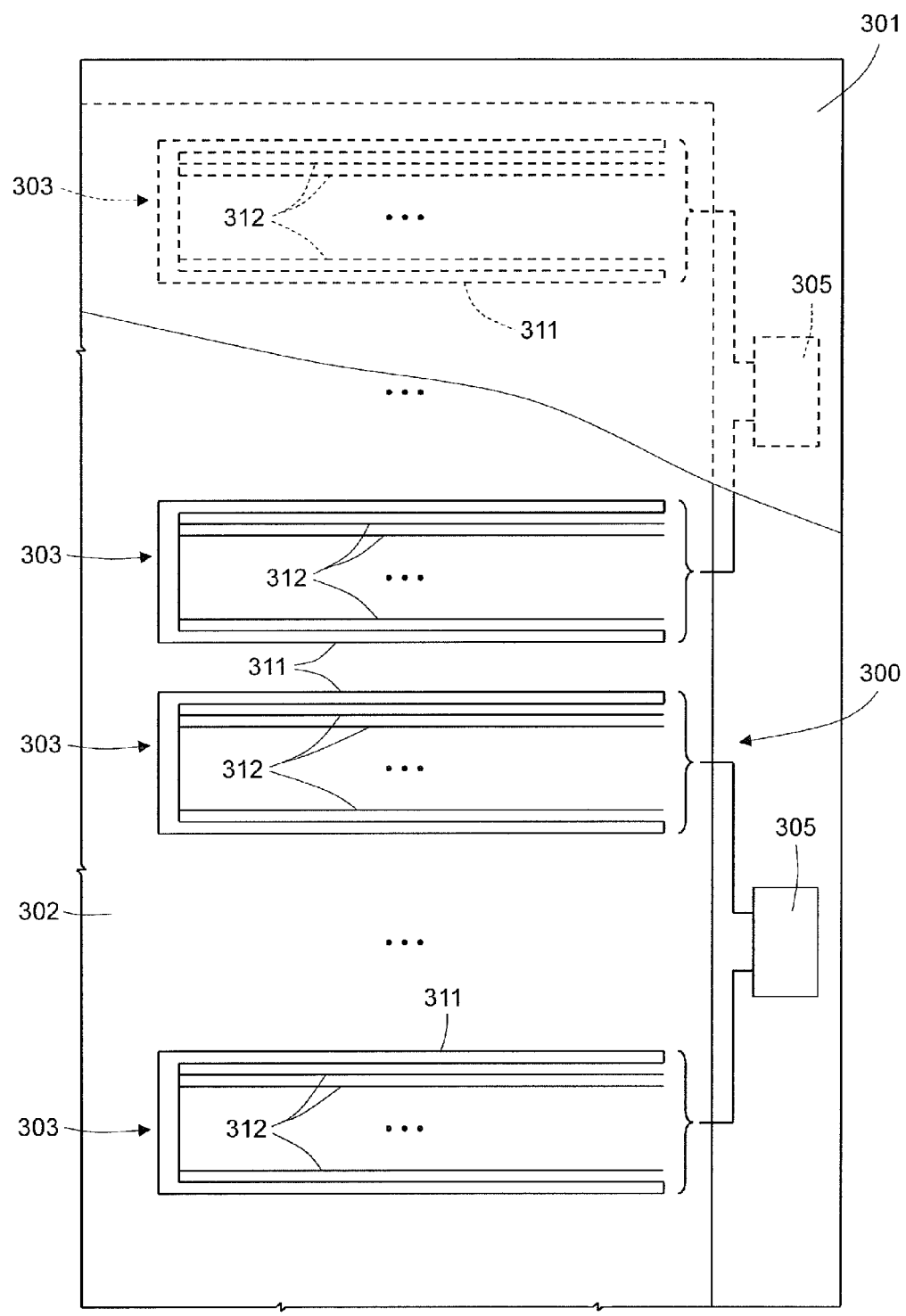
FIG. 12 shows a top plan view of a portion of a mattress incorporating a sensor for pressure measurements, according to another embodiment of the present disclosure.

In the embodiment of FIG. 12, a sensor for pressure measurements 300 is incorporated in a mattress 301. In particular, the sensor 300 is arranged in a surface layer of the mattress 301 and comprises a support 302 of transparent insulating fabric, arranged on which are insulating structures 303, and a plurality of processing units 305.

The insulating structures 303 follow one another in a longitudinal direction of the mattress 301 and comprise respective reference tracks 311 and sense tracks 312. The sense tracks 312 extend in comb like fashion from the respective reference tracks 311 in a direction transverse to the longitudinal direction of the mattress 301 substantially throughout its width. Moreover, the sense tracks 312 are connected to respective processing units 305. More precisely, the processing units 305 serve respective groups of conductive structures 303, reading in rotation resistance values of the respective sense tracks 312.

In the embodiment of FIG. 12, the sensor advantageously covers practically the entire surface of the mattress 301, providing information on the distribution of the weight of the user during rest. The use of a transparent fabric for the support 302 makes it possible to provide the sensor 300 in a layer that is very close to the surface of the mattress 301 to obtain a higher sensitivity, without entailing trouble for the user.

Modifications and variations may be made to the sensor for pressure measurements described, without thereby departing from the scope of the present invention, as defined in the annexed claims. In particular, the conductive structures can extend along any track, with characteristics advantageously selected in relation to the type of application for which the sensor is used. Not necessarily does the arrangement of the conductive structures have to follow the warp or weave directions.

That which is claimed is:

1. A sensor for pressure measurement comprising:
    a fabric support;
    at least one electrically conductive structure comprising a plurality of tracks on said fabric support having resistance variations in response to deformations thereof; and
    a processor coupled to said at least one electrically conductive structure and configured to sense resistance values of respective tracks of said at least one electrically conductive structure to provide a signal representative of a pressure difference across opposite faces of said fabric support.

2. The sensor according to claim 1 wherein said plurality of tracks comprises a reference track extending in a first direction, and a plurality of sense tracks extending from said reference track in a comb-like pattern in a second direction.

3. The sensor according to claim 2 wherein said processor comprises a plurality of terminals; wherein each sense track has an end coupled to a respective terminal of said processor; and further comprising a plurality of connection lines coupling the ends of said plurality of sense tracks to said plurality of terminals.

4. The sensor according to claim 1 wherein said plurality of tracks comprises:
    a plurality of connection tracks defining a plurality of terminals; and
    a plurality of sense tracks configured to, with the pressure difference across the opposite faces of said fabric support in an operation interval, cause, between said plurality of terminals respective resistance variations falling in respective distinct and non-overlapping intervals.

5. The sensor according to claim 4 wherein said plurality of tracks comprises a resistive ladder network.

6. The sensor according to claim 4 wherein each sense track has opposite ends respectively coupled to said plurality of connection tracks; and wherein said plurality of sense tracks is arranged at respective locations in a first direction.

7. The sensor according to claim 6 wherein said at least one electrically conductive structure comprises a plurality thereof aligned along a second direction transverse to the first direction.

8. The sensor according to claim 1 wherein said fabric support comprises a plurality of warp yarns, and a plurality of weave yarns woven of dielectric material to form a mesh structure.

9. The sensor according to claim 8 wherein said fabric support has a same longitudinal elastic modulus in a warp direction and in a weave direction.

10. The sensor according to claim 9 wherein said plurality of warp yarns and said plurality of weave yarns have equal density.

11. The sensor according to claim 8 wherein said fabric support has a longitudinal elastic modulus in a warp direction different from a longitudinal elastic modulus in a weave direction.

12. The sensor according to claim 11 wherein said plurality of warp yarns and said plurality of weave yarns have different densities.

13. The sensor according to claim 11 wherein said plurality of warp yarns and said plurality of weave yarns comprise different materials.

14. The sensor according to claim 11 wherein each warp yarn has a different diameter with respect to each of said plurality of weave yarns.

15. The sensor according to claim 8 further comprising a layer of elastomeric material; and wherein said fabric support is embedded in said layer of elastomeric material.

16. The sensor according to claim 1 wherein said fabric support is permeable to fluids.

17. The sensor according to claim 1 wherein said processor comprises a processing module and a multiplexer configured to sequentially couple said plurality of tracks to said processing module.

18. A sensor for pressure measurement comprising:
    a fabric support;
    a plurality of electrically conductive tracks on said fabric support having resistance variations in response to deformations thereof; and
    a processor coupled to said plurality of electrically conductive tracks and configured to sense resistance values of respective electrically conductive tracks of said plurality thereof to provide a signal representative of a pressure difference across opposite faces of said fabric support.

19. The sensor according to claim 18 wherein said plurality of electrically conductive tracks comprises a reference track extending in a first direction, and a plurality of sense tracks extending from said reference track in a comb-like pattern in a second direction.

20. The sensor according to claim 19 wherein said processor comprises a plurality of terminals; wherein each sense track has an end coupled to a respective terminal of said processor; and further comprising a plurality of connection lines coupling the ends of said plurality of sense tracks to said plurality of terminals.

21. The sensor according to claim 18 wherein said plurality of electrically conductive tracks comprises:
    a plurality of connection tracks defining a plurality of terminals; and
    a plurality of sense tracks configured to, with the pressure difference across the opposite faces of said fabric support in an operation interval, cause, between said plurality of terminals respective resistance variations falling in respective distinct and non-overlapping intervals.

22. The sensor according to claim 21 wherein said plurality of electrically conductive tracks defines a resistive ladder network.

23. A method for making a sensor for pressure measurement, the method comprising:
    forming a plurality of electrically conductive tracks on a fabric support and having resistance variations in response to deformations thereof; and
    coupling a processor to the plurality of electrically conductive tracks to sense resistance values of respective electrically conductive tracks of the plurality thereof to provide a signal representative of a pressure difference across opposite faces of the fabric support.

24. The method according to claim 23 wherein the plurality of electrically conductive tracks comprises a reference track extending in a first direction, and a plurality of sense tracks extending from the reference track in a comb-like pattern in a second direction.

25. The method according to claim 24 wherein the processor comprises a plurality of terminals; wherein each sense track has an end coupled to a respective terminal of the processor; and further comprising a plurality of connection lines coupling the ends of the plurality of sense tracks to the plurality of terminals.

26. The method according to claim 23 wherein the plurality of electrically conductive tracks comprises:
    a plurality of connection tracks defining a plurality of terminals; and
    a plurality of sense tracks to, with the pressure difference across the opposite faces of the fabric support in an operation interval, cause, between the plurality of terminals respective resistance variations falling in respective distinct and non-overlapping intervals.

27. The method according to claim 26 wherein the plurality of electrically conductive tracks define a resistive ladder network.

28. The method according to claim 26 wherein each sense track has opposite ends respectively coupled to the plurality of connection tracks; and wherein the plurality of sense tracks is arranged at respective locations in a first direction.

29. The method according to claim 23 wherein the fabric support comprises a plurality of warp yarns, and a plurality of weave yarns woven of dielectric material to form a mesh structure.

* * * * *